United States Patent
Von Busch et al.

(10) Patent No.: US 8,315,810 B2
(45) Date of Patent: Nov. 20, 2012

(54) APPARATUS, METHOD, COMPUTER-READABLE MEDIUM, AND USE FOR THERAPY PLANNING IN TREATMENT OF A PATIENT

(75) Inventors: Heinrich Von Busch, Aachen (DE);
Bernd Schweizer, Herzogenrath (DE);
Jens Christoph Georgi, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 625 days.

(21) Appl. No.: 12/446,989

(22) PCT Filed: Nov. 6, 2007

(86) PCT No.: PCT/IB2007/054495
§ 371 (c)(1),
(2), (4) Date: Apr. 24, 2009

(87) PCT Pub. No.: WO2008/056322
PCT Pub. Date: May 15, 2008

(65) Prior Publication Data
US 2009/0292481 A1    Nov. 26, 2009

(30) Foreign Application Priority Data
Nov. 10, 2006 (EP) .................................. 06123815

(51) Int. Cl.
*G06F 19/00* (2011.01)
(52) U.S. Cl. ......................................... 702/19
(58) Field of Classification Search .................... 702/19; 435/7.1, 7.23; 514/214.02, 217; 424/131.1, 424/204.1
See application file for complete search history.

(56) References Cited

U.S. PATENT DOCUMENTS

| | | | |
|---|---|---|---|
| 7,668,662 B2 * | 2/2010 | Kroll et al. ...................... 702/19 |
| 2002/0037493 A1 | 3/2002 | Savvides et al. | |
| 2002/0095258 A1 | 7/2002 | Agur et al. | |
| 2005/0137165 A1 * | 6/2005 | Pilarski ........................... 514/54 |

FOREIGN PATENT DOCUMENTS

| | | |
|---|---|---|
| JP | 11006831 A | 1/1999 |
| WO | 0145556 A1 | 6/2001 |
| WO | 2005038454 A1 | 4/2005 |
| WO | 2006113987 A1 | 11/2006 |

OTHER PUBLICATIONS

Wang, C., et al.; Reticulated platelets predict platelet count recovery following chemotherapy; 2002; Transfusion; 42:368-374.

* cited by examiner

*Primary Examiner* — Bryan Bui

(57) ABSTRACT

An apparatus, method, system, computer-readable medium and use for individual patient therapy planning of diseases such as cancer for different therapy modalities, such as radiation therapy and chemotherapy is provided. A new aspect of the invention is that the degree of bone marrow depression of the patient is related to the count of immature blood platelets, which are measured before each treatment. Some embodiments of the invention provide an advantage allowing reducing the level of uncertainty in the prediction of the risk of bone marrow depression, and thus enabling to safely improve the therapy effect by an increase of the radiation dosage and/or chemical dosage to the individual patient while the risk for bone marrow depression is minimized.

20 Claims, 2 Drawing Sheets

APPARATUS, METHOD, COMPUTER-READABLE MEDIUM, AND USE FOR THERAPY PLANNING IN TREATMENT OF A PATIENT

FIELD OF THE INVENTION

This invention pertains in general to therapy planning, and more particularly to the determination of the dosage and timing of the administration of a therapeutic agent used in treatment of a patient.

BACKGROUND OF THE INVENTION

In radiation therapy and chemotherapy of cancer, the detrimental side effect of the therapy on the bone marrow and its functions often constitutes the dose-limiting factor. The bone marrow performs vital functions in the production of red blood cells, white blood cells, and blood platelets. The red blood cells are cells that carry oxygen to all the organs and tissues of the body. The white blood cells are responsible for fighting infection caused by germs. The blood platelets are small, disc shaped cells in the blood that are needed to form blood clots to control bleeding and bruising. Radiation therapy and chemotherapy often causes a reduction in the number of white blood cells, increasing the risk of the person of developing an infection. Likewise, a reduction in blood platelets may affect blood coagulation and hemostasis. Without a minimum function of the bone marrow, no medical patient can survive for a prolonged period of time. Bone marrow depression is an abnormal condition characterized by the inability of the bone marrow to produce normal amounts of white blood cells, red blood cells and platelets, and is as mentioned above a detrimental side effect in radiation therapy and chemotherapy. Accordingly, while higher doses of a chemical agent and/or radiation usually have greater anti-tumor effects, the imperative requirement to maintain bone marrow function imposes limits to applicable dose. The residual bone marrow reserve, i.e. the degree to which the bone marrow is able to continue functioning and to recover from damage as for instance inflicted by radiation therapy and chemotherapy, is subject to strong interpatient variability. It moreover depends on the treatment history of the patient.

In current therapy modalities, a wide safety margin in the administered dose of anti-tumor agents like radiation and/or a chemical medication has to be observed in order to ensure avoidance of bone marrow failure, even if this means for the majority of patients a significant reduction in the probability with which the therapy will achieve tumor control. Hence, an improved apparatus, method, computer-readable medium, and use for therapy planning would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above-mentioned problems by providing an apparatus, method, a computer-readable medium, and use according to the appended patent claims.

According to one aspect of the invention, an apparatus for medical therapy planning in treatment of a patient is provided. The apparatus comprises a count unit for obtaining a count of immature blood platelets in said patient, a first calculation unit for calculating the eligibility of said patient for at least one therapy modality, based on said immature blood platelet count, and a second calculation unit for calculating an individual patient dosage plan of at least one therapeutic agent, based on said calculated eligibility of the patient.

According to another aspect of the invention, a method for medical therapy planning in treatment of a patient is provided. The method comprises obtaining a count of immature blood platelets in said patient, calculating the eligibility of said patient for at least one specific therapy modality, based on said immature blood platelet count, and calculating an individual patient dosage plan of at least one therapeutic agent, based on said calculated eligibility of the patient.

According to yet another aspect of the invention, a computer-readable medium for medical therapy planning in treatment of a patient is provided, the computer-readable medium having embodied thereon a computer program for processing by a processor. The computer program comprises a count code segment for obtaining a count of immature blood platelets in said patient, a first calculation code segment for calculating the eligibility of said patient for at least one specific therapy modality, based on said immature blood platelet count, and a second calculation code segment for calculating an individual patient dosage plan of at least one therapeutic agent, based on said calculated eligibility of the patient.

In a further aspect of the invention, a use of the apparatus, method and computer-readable medium according to any one of the appended claims is provided, for treatment of cancer.

Use of the invention according to some embodiments allows to reduce the level of uncertainty in the prediction of the risk of bone marrow depression, and thus makes it possible to safely improve the therapy effect by an increase of the radiation dosage and/or chemical dosage to the individual patient while the risk for bone marrow depression is kept minimal.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Figure 1:
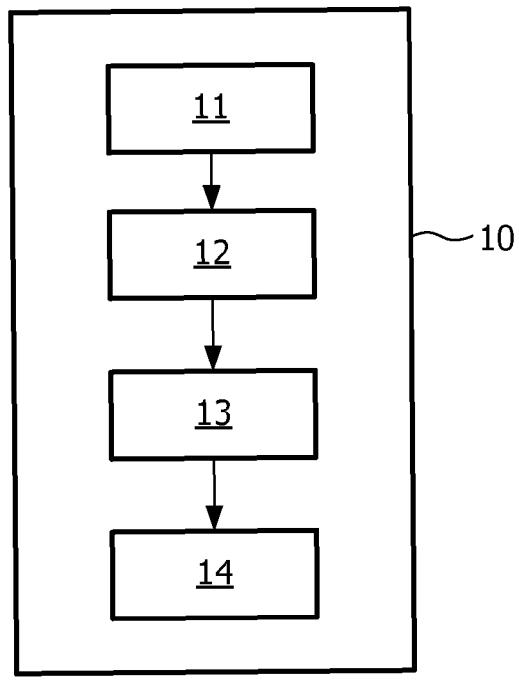
FIG. 1 is a block diagram of an apparatus according to an embodiment.

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting for the invention.

The present invention provides according to some embodiments an apparatus, method, system, computer-readable medium and use for individual patient therapy planning of diseases such as cancer for different therapy modalities, such as radiation therapy and chemotherapy. Some embodiments allow for increased treatment efficacy, flexibility, cost-effectiveness, and patient comfort.

A new aspect of the invention is that the degree of bone marrow depression of the patient is related to the count of immature blood platelets, which are measured before each treatment. In the bone marrow, red and white blood cells and blood platelets are formed. These cells and platelets have a lifetime of approximately 120 days for red blood cells, and approximately 8-10 days for blood platelets. Counting their numbers in the blood thus reflects the activity that the bone marrow had days or weeks before. The cells and platelets usually mature in the bone marrow, however small amounts of immature platelets and cells are present in the blood as well, and their counts reflect the bone marrow viability with much reduced delay. Hence, the immature platelets and cells represent a far more immediate measure of the bone marrow function than that of mature platelets and cells. White blood cells counts strongly vary as a result of immune responses, and red blood cells take 7 days to develop and may moreover vary in number because of altitude and other factors, so that immature platelets represent the best option as an immediate measure of bone marrow viability.

Another new aspect of the invention is to use the count of the immature blood platelets to calculate a risk of bone marrow depression for calculating an individual patient dosage plan for the most suitable therapeutic agent(s) and therapy modality(ies).

Some embodiments of the invention provide an advantage by allowing to reduce the level of uncertainty in the prediction of the risk of bone marrow depression, and thus making it possible to safely improve the therapy effect by an increase of the radiation dosage and/or chemical dosage to the individual patient while the risk for bone marrow depression is kept minimal.

The following description focuses on embodiments of the present invention applicable to medical imaging and in particular to therapy planning for the treatment of cancer. However, it will be appreciated that the invention is not limited to this application but may be applied to many other diseases including for example immunosuppression in the treatment of autoimmune diseases.

In an embodiment an apparatus 10, according to FIG. 1, for medical therapy planning in a therapy is provided. The apparatus comprises a count unit 11 for obtaining, e.g. measuring, a count of immature blood platelets in a patient, a first calculation unit 12 for calculating the risk of bone marrow depression, as a consequence of using a therapy modality in dependence on the immature blood platelet count, a second calculation unit 13 for calculating an individual patient dosage plan of a therapeutic agent used in said therapy, based on the risk of bone marrow depression.

In an embodiment the therapeutic agent is carboplatin and the therapy modality is chemotherapy.

In an embodiment the first calculation unit utilizes parameters, such as, but not limited to, body weight, size, blood parameters, and anatomical and/or functional imaging data in combination with the count of immature blood platelets, for calculating the risk of bone marrow depression for a specific therapy modality. These parameters may be stored and/or retrieved from an individual patient database. The individual patient database may be part of the individual patient journal, which contains the patient treatment history and other information regarding the patient status, such as medications, and general patient status, etc. that is used by the healthcare staff.

By calculating the risk of bone marrow depression, the first calculation unit in reality checks the eligibility for treatment with a certain therapeutic agent(s) and therapy modality(ies).

In an embodiment the first calculation unit is configured to check the eligibility for treatment with various therapeutic agents based on the current level of bone marrow function as reflected by the immature blood platelet count. An advantage of this embodiment is that the apparatus may be used to facilitate the decision which therapeutic agent, and thus therapy modality, may be utilized without excessive risk of bone marrow depression.

Another advantage of this embodiment is that in therapy modalities using several therapeutic agents, the most effective combination of therapeutic agents may be provided.

In an embodiment the calculated individual patient dosage plan comprises doses of the therapeutic agent(s) and/or the times between administrations of the therapeutic agent(s).

In an embodiment the second calculation unit the calculated individual patient dosage plan further comprises information regarding the estimated immature blood platelet count as a function of time following treatment using the doses and time between administrations for the therapeutic agent(s) calculated in the dosage plan.

In an embodiment the apparatus further comprises a re-planning unit 14 that is capable of re-planning the individual patient dosage plan. The re-planning unit may take into account the history of calculated individual patient dosage plans. In practice this means that the apparatus first calculates an individual patient dosage plan containing doses and time between administrations. Subsequently, in between administrations the count unit obtains a new measurement(s) of the immature blood platelet count of the patient at a certain point in time. This measured immature blood platelet count at the certain point in time is then compared to the estimated blood platelet count at the same point in time, wherein the estimated blood platelet count is comprised in the individual patient dosage plan. In an embodiment the re-planning unit takes into account two subsequently calculated individual patient dosage plans for the modification of the current individual patient dosage plan.

In an embodiment the re-planning unit takes into account, among other monitoring data such as standard blood parameters for the additional information of the physician supervising the treatment, a new measurement of the immature blood platelet count.

In an embodiment the first calculation unit calculates a ratio, $r_{el}$, between the individual patient immature blood platelet count $c_{ind}$ and the standard value $c_{st}$ in patients that are not bone marrow-impaired. The ratio $r_{el}$ is then compared to a therapy modality specific minimum acceptable value of $r_{el,min}(x,y)$. If $r_{el}$ exceeds $r_{el,\ min}(x,y)$, the bone marrow depression resulting from the specific therapy is predicted to be non-critical. Different therapy modalities x with different therapeutic agents y have different minimum ratios $r_{el,min}(x,y)$. Moreover, lower ratios $r_{el}$ will translate into lower doses and longer times in between administrations, thereby reducing the stress inflicted on the blood marrow and allowing longer recovery times. As an example, if the standard dose for patients with normal blood platelet precursor counts $c_{st}$ is $d_{st}$ and the standard time in between administrations is $t_{st}$, the individual patient with a platelet count $c_{ind}=r_{el}*c_{st}$ will be considered eligible for a specific therapeutic agent y and therapy modality x if $r_{el}$ is larger than a predetermined threshold value $r_{el,min}(x,y)$. $r_{el,\ min}(x,y)$ is specific for each therapy modality. A $r_{el}$ lower than $r_{el,\ min}(x,y)$ signifies that the bone marrow function is reduced compared to normal healthy persons to such a low level that the combination of therapy modality x and agent y should not be applied at all. One implementation of an eligibility check then is to verify that $r_{el} \geq r_{el,min}$. If $r_{el}$ is in between $r_{el,min}(x,y)$ and 1, and extending to values >1, dose and/or times in between administrations may be adapted using the second calculation unit.

In a typical embodiment, dose will be interpolated linearly between 0 for $r_{el}=r_{el,min}(x,y)$ and the standard dose for $r_{el}=1$. Likewise, the time between administrations may be interpolated in an inversely linear fashion between infinity for $r_{el}=r_{el,min}(x,y)$ (meaning that administration of a dose is not repeated at all) and the standard interval for $r_{el}=1$. Modifications of dose and time between administrations may also be combined. Moreover, it should be appreciated that $r_{el}$ represents a patient-specific measure and that $r_{el,min}(x,y)$ is a therapy-specific limit. In this way the first calculation unit may check eligibility for several different therapeutic agents and therapy modalities for each individual patient.

In an embodiment the first calculation unit is configured to select a therapeutic agent and therapy modality with the highest ratio $r_{el}$ compared to $r_{el,min}(x,y)$ for the individual patient.

The information regarding the selected therapeutic agent and/or therapy modality is then utilized by the second calculation unit to calculate a dosage plan for the selected therapeutic agent. As an example, the dosage $d_{ind}$ is calculated as $d_{ind}=d_{st}*r_{el}$ and with times in between administrations of $t_{ind}=t_{st}/r_{el}$, wherein $t_{st}$ is a standard time between dosage administrations In an embodiment the re-planning unit is configured to update the rules used by the second calculation unit for the calculation of new patient dosage plans based on the new count of immature blood platelets as a result of the previous treatment cycle. This embodiment enables the apparatus to modify the calculation algorithm for new individual patient dosage plans, using experience-based changes in the rules. One way of calculating the individual patient dosage plan is based on the assumption that there is a continuum of degrees of bone marrow depression between bone-marrow-healthy and bone-marrow-depressed individuals, and that such a degree of bone marrow depression is characterized by the ratio $r_{el}$ that is obtained by division of the immature blood platelet count in the individual patient by that of a bone-marrow-healthy person. Accordingly, one way of implementing said rules used by the second calculation unit is to interpolate, in the range between $r_{el}=1$ and the therapy-modality-specific minimum acceptable level $r_{el,min}$ of the parameter $r_{el}$ the dose/time between administrations linearly/inversely linearly to $r_{el}$. One way of implementing experience-based changes in the rules may be a deviation from said linear/inversely linear interpolation of dose/time between administrations.

If a new patient is about to receive treatment using the apparatus according to some embodiments of the invention, a reference model comprising parameter estimates initially suitable for most patients will be used by the second calculation unit together with the immature blood platelet count of the patient for the calculation of a first individual patient dosage plan.

In an embodiment the initially estimated parameters of the reference model may be updated based on comparing the measured immature blood platelet count and the predicted immature blood platelet count for a specific therapy. The updated parameter estimates of the reference model better describe an average patient and allow calculating a more accurate first individual patient dosage plan for a new patient for a specific therapy.

If a patient has already received treatment using an individual patient dosage plan calculated by the apparatus according to some embodiments, the existing individual patient dosage plan will be updated using a new immature blood platelet count.

In an embodiment the therapy modality is a targeted therapy of non-Hodgkin's lymphoma.

In an embodiment the first calculation unit is configured to calculate the risk of bone marrow depression for several therapy modalities to find the therapy modality that will be most effective for the individual patient based on the individual patient's immature platelet count.

In an embodiment the therapeutic agents is Rituxan®/90Y-Zevalin® comprising cold and hot anti-CD20 targeted therapeutic agents. Both Rituxan® and $^{90}$Y-Zevalin® are monoclonal antibodies targeted to the CD20 receptor of B-cells. While Rituxan® is active on its own simply by attaching to the CD20 receptor of B-cells, $^{90}$Y-Zevalin® not only attaches to the receptor, but also carries a radioactive label ($^{90}$Y) that provides additional destructive action by emission of a beta particle. In Zevalin® therapy, Rituxan® is administered prior to the Zevalin® agent proper in order to saturate non-specific binding sites and to improve, i.e. make more specific, the biodistribution of the Zevalin® agent itself.

In this case, in a practical implementation, on the basis of the measurement of the immature platelet count of the individual patient, non-critical bone marrow depression is predicted for the targeted therapy of non-Hodgkin's lymphoma. The second calculation unit then calculates an individual patient dosage plan for Rituxan®/$^{90}$Y-Zevalin® therapy, giving a recommendation for both the Rituxan® and $^{90}$Y-Zevalin® anti-CD20 antibody doses to be administered.

In an embodiment wherein the therapy modality x is chemotherapy of bronchial carcinoma and the therapeutic agent y is carboplatin, $r_{el,min}(x,y)$ is 0.3. Thus, if the measured individual patient blood platelet count divided by the standard count of immature blood platelets in normal patients is higher than this value the individual patient will be eligible for the therapy modality and therapeutic agent.

In an embodiment wherein the therapy modality x is targeted radiotherapy of non-Hodgkin's lymphoma and the therapeutic agent y is Rituxan®/$^{90}$Y-Zevalin®, $r_{el,min}(x,y)$ is 0.5.

In another embodiment wherein the therapy modality is external radiation therapy, the optimization of the dose plan is adapted to the bone marrow status of the individual patient by introducing the requirement in the treatment planning optimization that the maximum permitted dose to bone-marrow containing non-target regions is reduced, relative to the corresponding dose limit in bone-marrow-healthy subjects, by multiplication with $r_{el}$.

In an embodiment the first calculation unit is configured to select several therapeutic agents and/or therapy modalities meeting the requirements of $r_{el}$ compared to $r_{el,min}(x,y)$. A combination treatment may in some cases be more effective than treatment using only one therapeutic agent. In this embodiment the second calculation unit may be configured to calculate a dosage plan for each used therapeutic agent by weighting each therapeutic agent dosage in regard to the total effect of the dosage for all used therapeutic agents.

In an embodiment the calculated dosage plan includes a recommendation on the therapy of choice by comparison, and a plan for the total dose to be administered, the fractionation scheme, and the exact way of administration, such as spatial distribution in external radiation therapy and administration pathway in targeted radiation therapy and chemotherapy.

The first calculation unit, second calculation unit, and re-planning unit may be any unit normally used for performing the involved tasks, e.g. a hardware, such as a processor with a memory. The processor may be any of variety of processors, such as Intel or AMD processors, CPUs, microprocessors, Programmable Intelligent Computer (PIC) microcontrollers, Digital Signal Processors (DSP), etc. However, the scope of the invention is not limited to these specific processors. The memory may be any memory capable of storing information, such as Random Access Memories (RAM) such as, Double Density RAM (DDR, DDR2), Single Density RAM (SDRAM), Static RAM (SRAM), Dynamic RAM (DRAM), Video RAM (VRAM), etc. The memory may also be a FLASH memory such as a USB, Compact Flash, SmartMedia, MMC memory, MemoryStick, SD Card, MiniSD, MicroSD, xD Card, TransFlash, and MicroDrive memory etc. However, the scope of the invention is not limited to these specific memories.

In an embodiment the first calculation unit is a computer having software that implements models of the risk of bone marrow depression in dependence on the immature blood platelet count.

In an embodiment the apparatus comprises units for performing the method according to some embodiments.

In an embodiment the apparatus is comprised in a medical workstation or medical system, such as a Computed Tomography (CT) system, Magnetic Resonance Imaging (MRI) System, Ultrasound Imaging (US) system, radiation therapy system or chemotherapy system.

Figure 2:
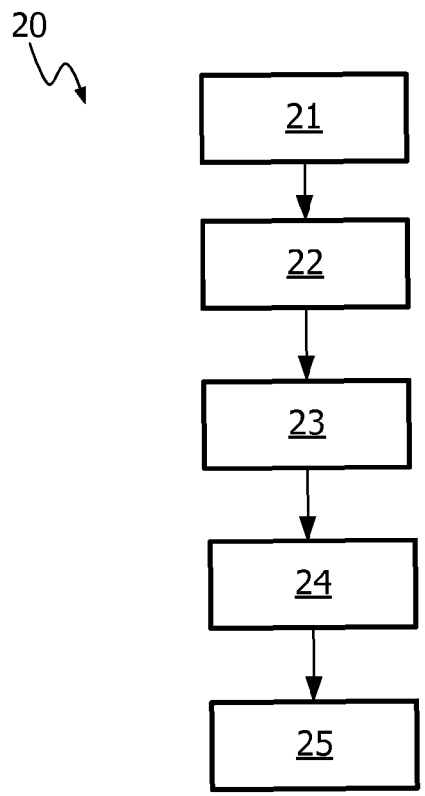
FIG. 2 is a block diagram of a method according to an embodiment.

In an embodiment, according to FIG. 2, a method for medical therapy planning in treatment of a patient is provided. The method comprises counting 21 the immature blood platelets in said patient, calculating 22 the eligibility of said patient for at least one specific therapy modality, based on said immature blood platelet count, and calculating 23 an individual patient dosage plan of at least one therapeutic agent, based on said calculated eligibility of the patient.

In an embodiment the method further comprises re-planning 24 said individual patient dosage plan by comparing a new count of the immature blood platelets with an estimated immature blood platelet count being comprised in said individual patient dosage plan.

In an embodiment the method further comprises updating 25 said calculating an individual patient dosage plan for a new patient based on said new immature blood platelet count compared to said estimated immature blood platelet count.

Figure 3:
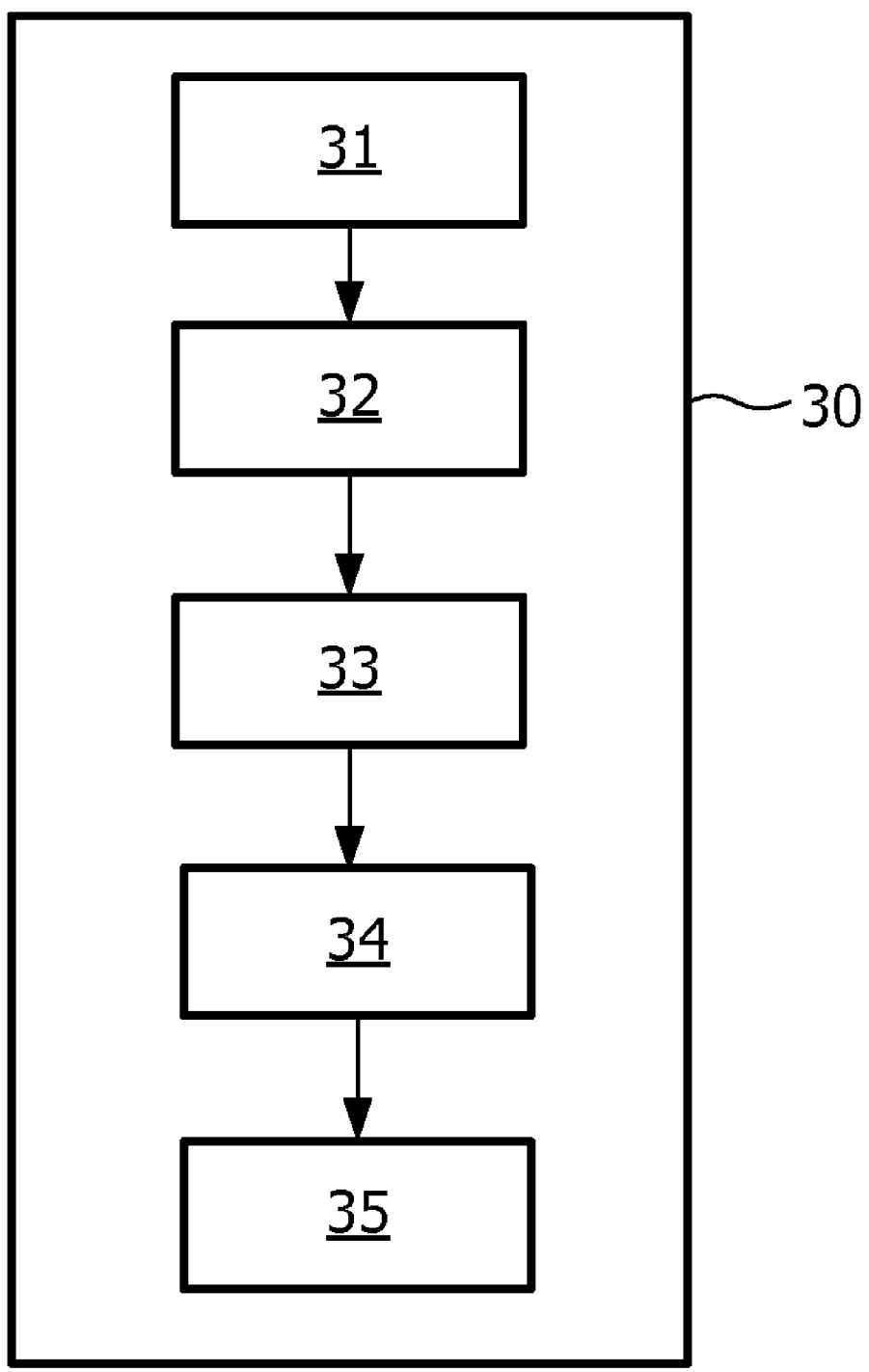
FIG. 3 is a block diagram of a computer-readable medium according to an embodiment.

In an embodiment, according to FIG. 3, a computer-readable medium 30 for medical therapy planning in treatment of a patient is provided, the computer-readable medium having embodied thereon a computer program for processing by a processor. The computer program comprises a count code segment 31 for obtaining a count of immature blood platelets in said patient, a first calculation code segment 32 for calculating the eligibility of said patient for at least one specific therapy modality, based on said immature blood platelet count, and a second calculation code segment 33 for calculating an individual patient dosage plan of at least one therapeutic agent, based on said calculated eligibility of the patient.

In an embodiment a computer-readable medium further comprises a re-planning code segment 34 for re-planning said individual patient dosage plan by comparing a new count of the immature blood platelets with an estimated immature blood platelet count being comprised in said individual patient dosage plan.

In an embodiment the computer-readable medium further comprises an update code segment 35 for updating said calculation of an individual patient dosage plan for a new patient based on said new immature blood platelet count compared to said estimated immature blood platelet count.

In an embodiment the apparatus, method and computer-readable medium according to any of the embodiments are used for the treatment of cancer.

In an embodiment the computer-readable medium comprises code segments arranged, when run by an apparatus having computer-processing properties, for performing all of the method steps defined in some embodiments.

Applications and use of the above-described embodiments according to the invention are various and include exemplary fields such as radiation therapy planning. However, the applications of the invention clearly extend beyond radiation therapy to chemotherapies and combined therapies.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different diseases, such as autoimmune diseases, than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. An apparatus for medical therapy planning in treatment of a patient, said apparatus comprising:
   a count unit which obtains a count of immature blood platelets in said patient,
   a first calculation unit which calculates a degree of bone marrow depression based on said immature blood platelet count relative to a minimum degree associated with at least one specific therapy modality, and based on the calculated degree of bone marrow depression, determining eligibility of said patient for said at least one therapy modality, and
   a second calculation unit which calculates an individual patient dosage plan of at least one therapeutic agent, based on said eligibility of said patient.

2. The apparatus according to claim 1, wherein said first calculation unit is arranged to calculate the degree of bone marrow depression to determine eligibility based on the ratio between said immature blood platelet count of said patient and a standard immature blood platelet count for a healthy human without bone marrow depression.

3. The apparatus according to claim 1, wherein said calculated individual patient dosage plan comprises:
a dose of said at least one therapeutic agent; and
the time between administrations of said at least one therapeutic agent.

4. The apparatus according to claim 1, wherein said second calculation unit further is arranged for estimating the immature blood platelet count as a function of time for said patient following treatment according to said individual patient dosage plan.

5. The apparatus according to claim 4, further comprising:
a re-planning unit configured to re-plan said individual patient dosage plan by comparing a new count of the immature blood platelets with said estimated immature blood platelet.

6. The apparatus according to claim 5, wherein said dosage is increased or said time between administrations is decreased if said new count of immature blood platelets is higher than said estimated immature blood platelet count, and vice versa.

7. The apparatus according to claim 5, wherein said re-planning unit is configured to update the calculation of new individual patient dosage plans, performed by said second calculation unit, based on said new immature blood platelet count compared to said estimated immature blood platelet count.

8. The apparatus according to claim 1, wherein said at least one therapy modality is targeted therapy of non-Hodgkin's lymphoma, and said at least one therapeutic agent is Rituximab/90Y-Zevalin®.

9. The apparatus according to claim 1, wherein said at least one therapy modality is chemotherapy, and said at least one therapeutic agent is carboplatin.

10. The apparatus according to claim 1, wherein said first calculation unit is configured to calculate the risk of bone marrow depression for several therapy modalities based on said immature blood platelet count, and to select a therapy modality from the several therapy modalities based on the calculated risk.

11. The apparatus according to claim 1 being comprised in a medical workstation or medical system.

12. A method for medical therapy planning in treatment of a patient, said method comprising:
obtaining a count of immature blood platelets in said patient,
checking, with one or more processors, eligibility of said patient for at least one specific therapy modality, based on a current level of bone marrow function as reflected by said immature blood platelet count relative to a minimum bone marrow function associated with said at least one specific therapy modality, and
calculating an individual patient dosage plan of at least one therapeutic agent, based on said eligibility of the patient.

13. A method according to claim 12, wherein the individual dosage plan is calculated for cancer treatment planning.

14. A method according to claim 12, further comprising estimating an immature blood platelet count as a function of time for said patient following treatment according to said individual patient dosage plan.

15. The method according to claim 14, further comprising re-planning said individual patient dosage plan by comparing a new count of the immature blood platelets with the estimated immature blood platelet count being comprised in said individual patient dosage plan.

16. The method according to claim 15, further comprising updating a reference model comprising parameter estimates suitable for calculating a first individual patient dosage plan for a new patient based on said comparing new immature blood platelet count to said estimated immature blood platelet count.

17. A non-transitory computer readable storage medium carrying software which controls one or more computers to:
obtain a count of immature blood platelets in a patient,
determine eligibility of said patient for at least one specific therapy modality by calculating a risk of bone marrow depression based on said immature blood platelet count relative for said at least one specific therapy modality, and
calculate an individual patient dosage plan of at least one therapeutic agent, based on said eligibility of the patient.

18. A method for medical therapy planning in treatment of a patient, said method comprising:
measuring a count of immature blood platelets in said patient;
calculating a patient-specific ratio between the count of immature blood platelets in said patient and a standard immature blood platelet count value in patients that are not bone marrow-impaired;
with one or more processors, comparing the calculated patient-specific ratio to at least one minimum acceptable therapy-specific value associated with a corresponding therapy modality stored in memory associated with the one or more processors, so as to confirm the eligibility of said patient for said corresponding therapy modality; and
calculating an individual patient dosage plan of at least one therapeutic agent, based on said calculated ratio and said eligibility of the patient for said corresponding therapy modality.

19. The method of claim 18, further comprising selecting said at least one therapeutic agent and said at least one therapy modality for which said patient is eligible having the highest calculated ratio compared to the at least one minimum acceptable therapy-specific value for said at least one therapy modality.

20. The method of claim 19, wherein calculating the individual patient dosage plan further comprises:
calculating a dosage of said selected therapeutic agent for said patient based on a standard dosage and the calculated ratio; and
calculating a dosage schedule of said selected therapeutic agent for said patient based on a standard time between dosage administrations and the calculated ratio.

* * * * *